United States Patent [19]

Sakai et al.

[11]  4,216,284

[45]  Aug. 5, 1980

[54] COLOR PHOTOGRAPHIC LIGHT-SENSITIVE MATERIAL

[75] Inventors: Tadao Sakai; Masayoshi Kawai, both of Minami-ashigara; Tadao Shishido, Fujimiya, all of Japan

[73] Assignee: Fuji Photo Film Co., Ltd., Minami-ashigara, Japan

[21] Appl. No.: 837,977

[22] Filed: Sep. 29, 1977

Related U.S. Application Data

[63] Continuation-in-part of Ser. No. 645,136, Dec. 29, 1975, abandoned.

[30] Foreign Application Priority Data

Dec. 27, 1974 [JP] Japan ................................. 50/680

[51] Int. Cl.$^2$ ................................................. G03C 7/24
[52] U.S. Cl. ................................. 430/140; 430/448; 430/505; 430/566
[58] Field of Search .................... 96/10, 73, 74, 108, 96/95, 39, 4

[56] References Cited

U.S. PATENT DOCUMENTS

| | | | |
|---|---|---|---|
| 3,625,698 | 12/1971 | Sakazume | 96/108 |
| 3,705,799 | 12/1972 | Bello et al. | 96/74 |
| 3,705,801 | 12/1972 | Holtz | 96/74 |
| 3,723,125 | 3/1973 | Hayashi et al. | 96/74 |
| 3,730,724 | 5/1973 | Abbott | 96/74 |
| 3,765,901 | 10/1973 | Schellekens et al. | 96/95 |
| 3,895,948 | 7/1975 | Shiba et al. | 96/95 |
| 3,964,905 | 6/1976 | Hirose et al. | 96/39 |

OTHER PUBLICATIONS

The Theory of the Photographic Process, Mees and James, 3rd Ed., Macmillan Company, N.Y., (1967), pp. 521–523.
Photographic Science Engineering, DIR Couplers in Color Photography, Barr et al., vol. 13, No. 2, (1969), pp. 74–78.

*Primary Examiner*—J. Travis Brown
*Attorney, Agent, or Firm*—Sughrue, Rothwell, Mion, Zinn and Macpeak

[57] ABSTRACT

A color photographic light-sensitive material which comprises a support having coated thereon at least one light-sensitive silver halide emulsion layer containing a yellow dye-forming coupler, at least one light-sensitive silver halide emulsion layer containing a cyan dye-forming coupler, at least one light-sensitive silver halide emulsion layer containing a magenta dye-forming coupler and at least one light-sensitive silver halide emulsion layer containing at least one non-diffusible silver bleach inhibitor selected from the group consisting of a nitrogen-containing heterocyclic compound having a thioether bond and a heterocyclic compound containing one or more nitrogen atoms which combine with a group containing 11 or more carbon atoms to form a quaternary salt, in combination with one or more heterocyclic thione compounds having a thione group which is not capable of forming a mercaptan. The color photographic light-sensitive material provides silver images for sound recording without any specific processing steps as are conventionally used to form sound tracks.

4 Claims, No Drawings

COLOR PHOTOGRAPHIC LIGHT-SENSITIVE MATERIAL

This is a continuation-in-part of application Ser. No. 645,136, filed Dec. 29, 1975, now abandoned.

BACKGROUND OF THE INVENTION

1. FIELD OF THE INVENTION

The present invention relates to a color photographic light-sensitive material, more particularly, to a color photographic light-sensitive material capable of recording sound images.

In general, there are optical sound recording systems and magnetic sound recording systems as methods of recording sound images in color photographic light-sensitive materials for movie or television use. The present invention relates to a photographic material suitable for an optical recording system.

2. DESCRIPTION OF THE PRIOR ART

Sound images using an optical sound recording system in color photography such as a color print film, a color reversal film or a color reversal print film can be reproduced by converting a sound signal, which is recorded as changes in the density or areas in the color photograph, into a light signal, converting the light signal into an electric signal using a light acceptor and then converting the electric signal into a sound signal. In such reproduction, a phototube having various spectral characteristics is used as the light acceptor. The most commonly used phototube is an "S-1" type phototube which has a maximum spectral sensitivity at about 800 m$\mu$ in the infrared region (see, for example, Adrian Cornwell Clyne, Color Cinematography, page 593 (1951)).

On the other hand, the absorption maximum of dyes produced by the coupling reaction of a color coupler with the oxidation product of a developing agent such as p-phenylene-diamine is substantially within the visible region, and is inconsistent with the spectral characteristics of such a photo-tube. Thus, sound images due only to color dye images are very weak, and are not practical for use. Therefore, in order to reproduce practical sound images in color photographic light-sensitive materials, a silver image or silver sulfide image is usually formed on the sound track areas of the photographic material by specially processing the same, and the optical density of the images in the infrared region is utilized for sound reproduction. In this case, the optical density (transmittance density) in the infrared region is usually 1.0 to 1.6.

Sound track images in a color print film can be produced by the processing disclosed in, for example, *Journal of the Society of Motion Picture and Television Engineers,* Vol. 77, page 1154 (1968). According to this method, color images in the image portions and sound images in the sound track areas are simultaneously formed in the color development step. In a first fixing step, unexposed halide is removed, and in a bleaching step, the developed silver formed in the color developing step is rehalogenated. In a sound development step, the silver halide corresponding only to the sound track areas is converted into a silver image by selectively coating a viscous sound developer on the sound track areas. In a second fixing step the silver halide in the image portions is removed, and in a stabilizing step the color dye images are stabilized. The optical density in the infrared region of the silver images thus-formed on the sound track areas is used for sound reproduction.

As described above, processing steps for forming silver or silver sulfide images are used in the production of sound track images for color films. The reason why the sound track images composed of silver or silver sulfide are provided is that the maximum spectral sensitivity of a phototube conventionally used for sound reproduction is within the infrared region while color dye images formed by color processing do not have sufficient density in the infrared wavelength region. The step of forming silver or silver sulfide images in the sound track images is necessary in addition to the step of forming color dye images in the image portions. Therefore, a method for forming sound images in which these additional steps can be eliminated has been desired.

In order to eliminate the above problems, recently compounds have been proposed which can render developed silver less bleachable in a bleaching step, which can render developed silver unbleachable during a bleaching step or which render developed silver bleachable during the initial period of bleaching to a certain bleaching extent, but unbleachable after a certain extent of bleaching, such compounds being added to a silver halide emulsion layer of the color photographic light-sensitive material. Compounds capable of rendering silver less bleachable or unbleachable as above described are hereinafter referred to as a silver bleach inhibitor.

In general, a color photographic light-sensitive material is composed of a support having coated thereon silver halide emulsion layers in a superposed relationship, each layer being sensitive to a different spectral region. The photographic material is image-wise exposed and color developed to form color images and silver images therein, with the silver images being removed from the layers in a bleaching step and a fixing step.

Where a color photographic light-sensitive material has a layer capable of forming silver images which are not removable in the silver and silver halide removal step, and such a material is used to form a color photograph containing color dye images and silver images by a conventional color development, the silver images can be advantageously used as sound track areas.

However, it is difficult for a compound having a mercapto group, which is described as a silver bleach inhibitor in U.S. Pat. Nos. 3,715,208 and 3,737,312, to provide a high silver density due to a development inhibiting action or a chemical inhibiting action. That is, if a large amount of a silver bleach inhibitor as disclosed is added, the silver bleach inhibiting effect is increased but the amount of silver retained after bleaching is less because a lesser amount of silver is developed overall. If a small amount of the silver bleach inhibitor is added, the amount of developed silver on development is increased, but a lesser amount of silver is retained after bleaching due to a reduced silver bleach inhibiting effect. In both cases, it is difficult for a large amount of silver to be retained after bleaching.

SUMMARY OF THE INVENTION

One object of the present invention is to provide a color photographic light-sensitive material capable of providing a high image density in infrared regions without the necessity for additional steps to form a sound track as are used in conventional processing methods.

Another object of the present invention is to provide a high image density in infrared regions without the necessity for additional processing steps as are used in conventional processing methods using a photographic light-sensitive material having a sound track forming layer with a low silver content.

A still further object of the present invention is to provide a sound image of high sound quality without the necessity for the additional processing steps as are used in conventional processing methods using a photographic light-sensitive material having a sound track forming layer with a low silver content.

These objects of the present invention can be attained using a color photographic light-sensitive material having a sound track forming layer containing a non-diffusible silver bleach inhibitor selected from the group consisting of a nitrogen-containing heterocyclic compound having a thioether bond as described in U.S. Pat. No. 3,940,271 and a nitrogen-containing heterocyclic compound as described in British Pat. No. 1,429,108, in combination with a heterocyclic thione compound where the thione group is not capable of forming mercaptan.

That is, the present invention provides a color photographic light-sensitive material which comprises a support having coated thereon at least one light-sensitive silver halide emulsion layer containing a yellow dye-forming coupler, at least one light-sensitive silver halide emulsion layer containing a cyan dye-forming coupler, at least one light-sensitive silver halide emulsion layer containing a magenta dye-forming coupler and at least one light-sensitive silver halide emulsion layer containing at least one non-diffusible silver bleach inhibitor selected from the group consisting of a nitrogen-containing heterocyclic compound having a thioether bond represented by the following general formula (I):

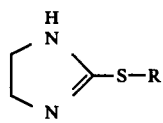

(I)

wherein R is an alkyl group having not less than 12 carbon atoms, with the alkyl group being both substituted or unsubstituted, and a heterocyclic compound containing one or more nitrogen atoms which combine with a group containing 11 or more carbon atoms to form a quaternary salt represented by the general formula (II):

(II)

wherein $Z_1$ is an atomic group necessary for forming a substituted or unsubstituted pyridine nuclei, imidazole nuclei or quinoline nuclei, $X^-$ is an anion, $R_1$ is a group having not less than 11 carbon atoms and is selected from the group consisting of (a) an alkyl group (e.g., substituted or unsubstituted), (b)

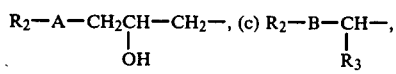

and (d)

$$R_2-A(C)_m-(D)_n-(CH_2CHCH_2)_p-,$$
$$\underset{OH}{|}$$

$R_2$ is an alkyl or alkylaryl group (e.g., substituted or unsubstituted), $R_3$ is a hydrogen atom or a methyl group, A is $-O-$, $-S-$, $-COO-$ or $-NCH_3-$, B is $-O-$, $-COO-$, $-CONH-$ or $-CONHC_2H_4CONH-$, C is an oxyalkylene group (such as an oxyethylene or oxypropylene group), D is $-CH_2CH_2-$ or $-O-$, m is an integer of 1 to 40, n is 0 or 1, and p is 0 or 1, in combination with at least one heterocyclic thione compound having a thione group which cannot form a mercaptan.

DETAILED DESCRIPTION OF THE INVENTION

According to one embodiment of the present invention, a color photographic light-sensitive material comprises a support having coated thereon a first silver halide emulsion layer containing a coupler which forms a yellow dye upon coupling with an oxidized color developing agent and which is sensitive to a first color region of the visible spectrum, a second silver halide emulsion layer containing a coupler which forms a cyan dye upon coupling with an oxidized color developing agent and which is sensitive to a second color region of the visible spectrum, a third silver halide emulsion layer containing a coupler which forms a magenta dye upon coupling with an oxidized color developing agent and which is sensitive to a third color region of the visible spectrum, and a fourth silver halide emulsion layer containing one or more silver bleach inhibitors selected from the group consisting of a nitrogen-containing heterocyclic compound having a thioether bond and a heterocyclic compound containing one or more nitrogen atoms which combine with a group containing 11 or more carbon atoms to form a quaternary salt, in combination with one or more heterocyclic thione compound having a thione group which cannot form a mercaptan and which is sensitive to the ultraviolet region, the visible region or the infrared region of the spectrum, wherein the layer arrangement is not limited.

When such a color photographic light-sensitive material is exposed from an original and color developed, yellow dye images and silver images are formed in the first silver halide emulsion layer, cyan dye images and silver images are formed in the second silver halide emulsion layer, magenta dye images and silver images are formed in the third silver halide emulsion layer, and silver images are formed in the fourth silver halide emulsion layer. In a subsequent bleaching, the silver images formed in the first, second and third silver halide emulsion layers are bleached, but the silver images formed in the fourth silver halide emulsion layer are not bleached due to the functions of the silver bleach inhibitor and the thione compound of the present invention. Thus, a color photograph containing color dye images and silver sound images is obtained. The above-described light-sensitive silver halide emulsion layer containing a silver bleach inhibitor and a thione compound according to the present invention is hereinafter often referred to as a sound track forming layer.

The fourth silver halide emulsion layer can be sensitive to the ultraviolet region, visible region or infrared region. However, the fourth silver halide emulsion layer must not form developed silver to such a degree which gives rise to an optical density undesirable for color reproduction. Accordingly, in the case where a sensitive region of the fourth silver halide emulsion layer overlaps that of the first, second or third silver halide emulsion layer, it is preferred that the sensitivity of the former be about 1/4, preferably 1/6 to 1/20, the sensitivity of the latter.

Alternatively, it is preferred that the sensitivity region of the fourth silver halide emulsion layer be provided in a sensitivity region between the first and second silver halide emulsion layers or between the second and third silver halide emulsion layers. In such a manner, the formation of an undesirable amount of silver in the fourth silver halide emulsion layer is prevented.

According to the present invention, the amount of coating silver in the sound track forming layer can be markedly reduced using a silver bleach inhibitor in combination with a heterocyclic thione compound having a thione group which cannot form a mercaptan (hereafter often merely referred to as the thione compound), as compared to using a silver bleach inhibitor alone. That is, the infrared density per unit weight of silver coated in the sound track forming layer can be remarkably increased compared with the situation where only a silver bleach inhibitor is used. Accordingly, the thickness of the sound track forming layer can be reduced and silver consumption lowered. Further, the decrease in the thickness of the sound track forming layer results in an improvement in the sharpness of the sound track, that is, an improvement in sound quality. Also, due to the decrease in the thickness of the sound track forming layer, scattering of light passed through the sound track forming layer is reduced and the sharpness of color image forming layers positioned nearer to the support than the sound track forming layer is improved.

A color photographic light-sensitive material of the present invention has at least one silver halide emulsion layer containing a silver bleach inhibitor and the thione compound as described in addition to a conventional blue-sensitive emulsion layer, a conventional green-sensitive emulsion layer and a conventional red-sensitive emulsion layer (the order of these layers is not limited).

One preferred embodiment of the present invention is a color photographic light-sensitive material comprising a support having coated thereon a blue-sensitive silver halide emulsion layer containing a yellow dye-forming coupler, a red-sensitive silver halide emulsion layer containing a cyan dye-forming layer, a green-sensitive silver halide emulsion layer containing a magenta dye-forming coupler and a green-sensitive silver halide emulsion layer (green-sensitive sound track forming layer) containing a silver bleach inhibitor and the thione compound, in this order from the support. Of course, the green-sensitive silver halide emulsion layer containing a silver bleach inhibitor and the thione compound can be positioned between the blue-sensitive silver halide emulsion layer containing a yellow dye-forming coupler and the red-sensitive silver halide emulsion layer containing a cyan dye-forming coupler or between the red-sensitive silver halide emulsion layer containing a cyan dye-forming coupler and the green-sensitive silver halide emulsion layer containing a magenta dye-forming coupler, and intermediate layers can be provided between each of these light-sensitive silver halide emulsion layers.

Another preferred embodiment of the present invention is a color photographic light-sensitive material comprising a support having coated thereon a red-sensitive silver halide emulsion layer containing a cyan dye-forming coupler, a green-sensitive silver halide emulsion layer containing a magenta dye-forming coupler, a yellow filter layer containing yellow colloidal silver or a yellow dye, a blue-sensitive silver halide emulsion layer containing a yellow dye-forming coupler and a green-sensitive silver halide emulsion layer containing a silver bleach inhibitor and the thione compound, in this order from the support. Of course, the silver halide emulsion layer containing a silver bleach inhibitor and the thione compound can be positioned between the yellow filter layer and the blue-sensitive silver halide emulsion layer containing a yellow dye-forming coupler, and intermediate layers can be provided between each of these light-sensitive silver halide emulsion layers. In either of these cases, the silver halide emulsion layer containing a silver bleach inhibitor and the thione compound can have spectral sensitivity in the ultraviolet, visible or infrared region.

A nitrogen-containing heterocyclic compound having a thioether bond which can be used as a bleach inhibitor in the present invention is represented by the following general formula (I):

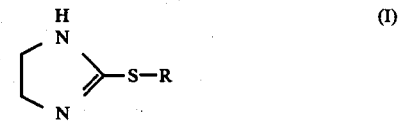

(I)

wherein R is an alkyl group having not less than 12 carbon atoms, with the alkyl group being both substituted or unsubstituted. Generally, an alkyl group having up to 20 carbon atoms can suitably be used. Suitably examples of such alkyl groups are dodecyl, tetradecyl, pentadecyl, hexadecyl, oleyl, octadecyl, etc., groups. Suitable substituents which can be present are alkoxy groups such as methoxy, ethoxy, etc., hydroxy, sulfo, carboxy, amino, etc.

An alkylimidazole compound represented by the general formula (I) can be in the free form or in a salt form. The salt can be formed using usual salt-forming agents such as hydrogen halides, perchloric acid, sulfuric acid, nitric acid, etc.

The following compounds are typical examples of compounds of the general formula (I).

| | | |
|---|---|---|
| (I-1) | imidazole-2-yl–S–$C_{12}H_{25}$ · HBr | (melting point, m.p. 81° C.) |
| (I-2) | imidazole-2-yl–S–$C_{16}H_{33}$ · HBr | (m.p. 96° C.) |
| (I-3) | imidazole-2-yl–S–$C_{16}H_{33}$ | (m.p. 91° C.) |
| (I-4) | imidazole-2-yl–S–$C_{12}H_{25}$ | (m.p. 87° C.) |

-continued (I-5) 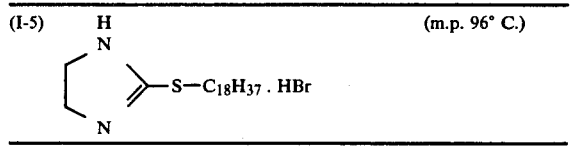 (m.p. 96° C.)

These compounds can be easily synthesized by the reaction of ethylene thiourea and an alkyl halide as described in *Analytical Chemistry*, Vol. 32, page 55 (1966).

A heterocyclic compound containing one or more nitrogen atoms which combine with a group containing 11 or more carbon atoms to form a quaternary salt which can be used as a bleach inhibitor in the present invention is represented by the following general formula (II):

 (II)

wherein $Z_1$ is an atomic group necessary for forming a substituted or unsubstituted pyridine nuclei, imidazole nuclei or quinoline nuclei, $X^-$ is an anion, $R_1$ is a group having not less than 11 carbon atoms and is selected from the group consisting of (a) an alkyl group (e.g., substituted or unsubstituted), (b)

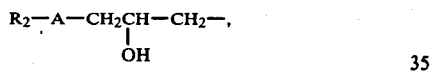

(c)

and (d)

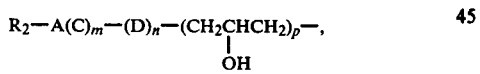

$R_2$ is an alkyl or alkylaryl group (e.g., substituted or unsubstituted), $R_3$ is a hydrogen atom or a methyl group, A is —O—, —S—, —COO— or —NCH$_3$—, B is —O—, —COO—, —CONH— or —CONHC$_2$H$_4$CONH—, C is an oxyalkylene group (such as an oxyethyene or oxypropylene group), D is —CH$_2$CH$_2$— or —O—, m is an integer of 1 to 40, n is 0 or 1, and p is 0 or 1. The pyridine nuclei, imidazole nuclei or quinoline nuclei can be unsubstituted or substituted as with substituents as shown in the specific examples of the compounds of this invention given hereinafter. Similarly, suitable examples of substituted alkyl groups for $R_1$ and alkyl and alkylaryl groups for $R_2$ are shown in the specific examples given hereinafter.

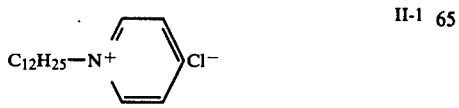 II-1

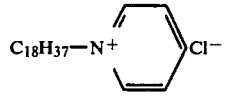 II-2

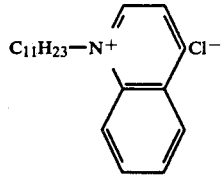 II-3

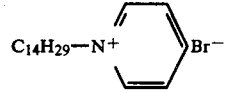 II-4

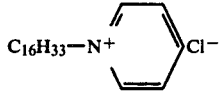 II-5

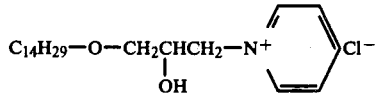 II-6

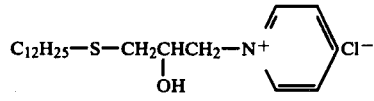 II-7

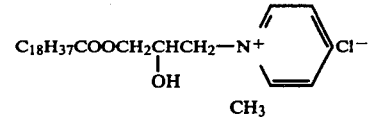 II-8

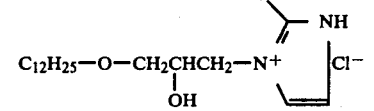 II-9

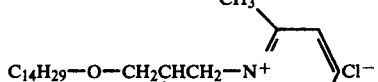 II-10

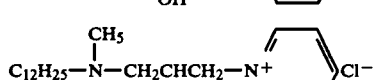 II-11

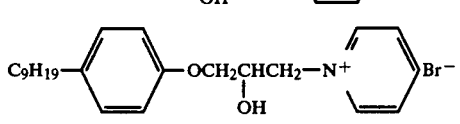 II-12

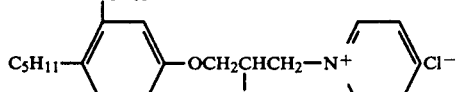 II-13

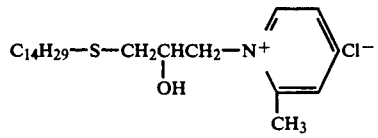 II-14

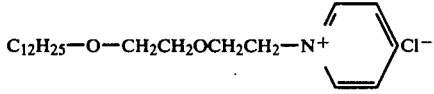 II-15

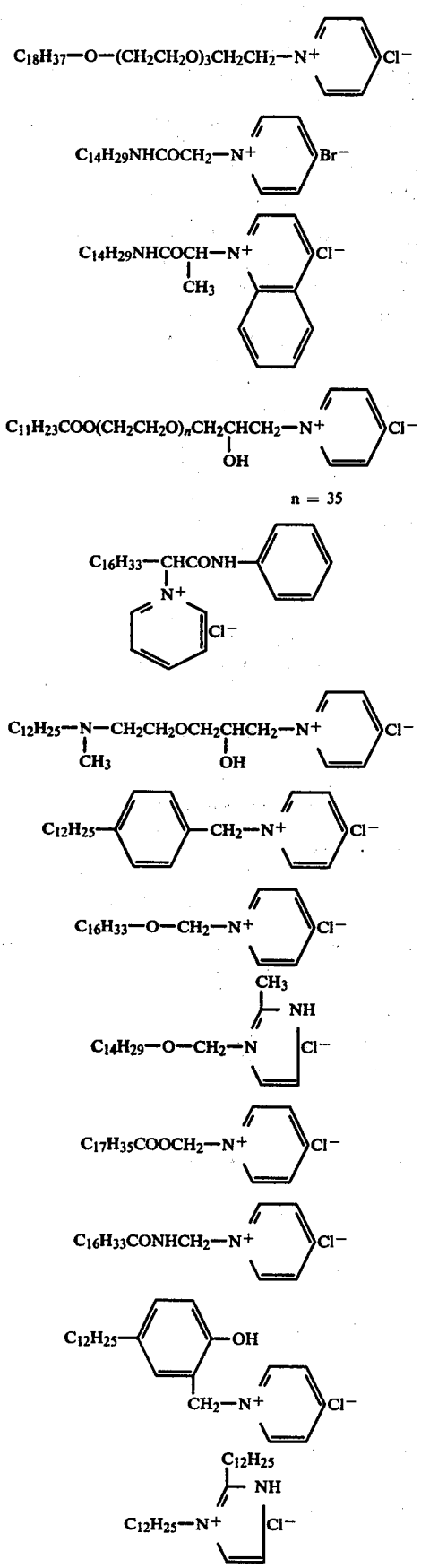
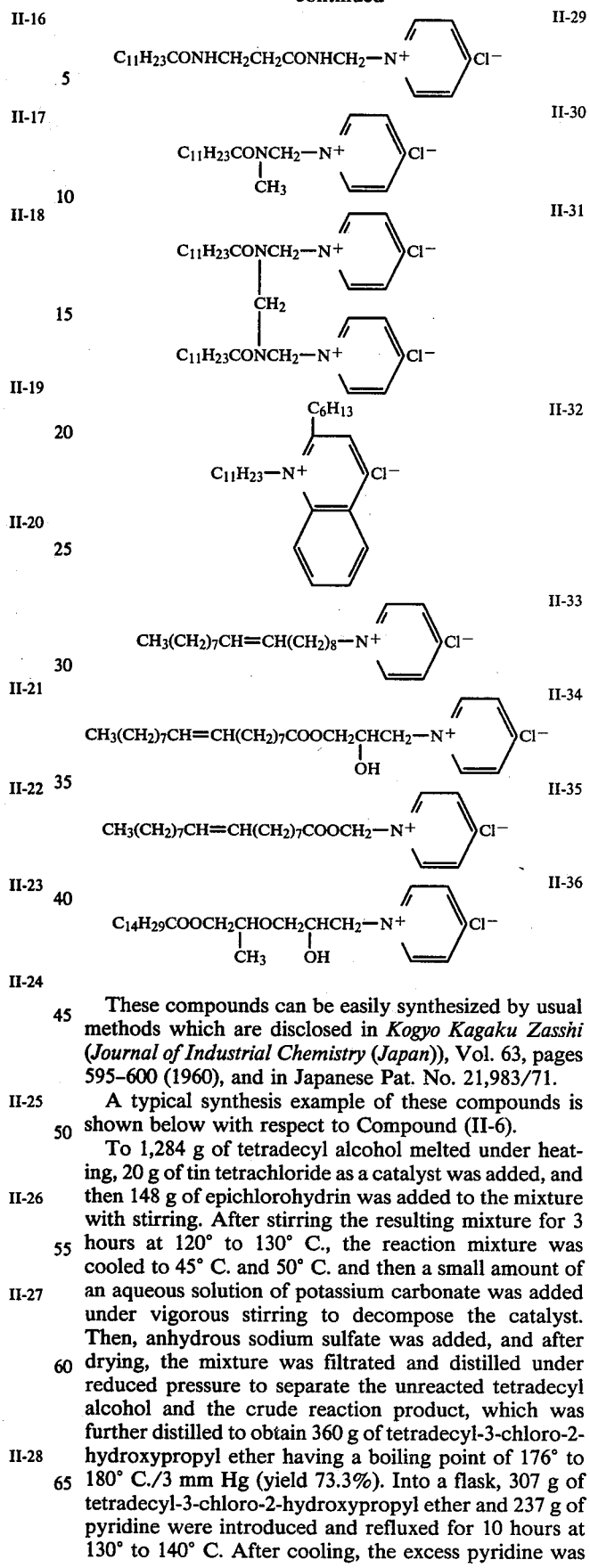

These compounds can be easily synthesized by usual methods which are disclosed in *Kogyo Kagaku Zasshi* (*Journal of Industrial Chemistry (Japan)*), Vol. 63, pages 595–600 (1960), and in Japanese Pat. No. 21,983/71.

A typical synthesis example of these compounds is shown below with respect to Compound (II-6).

To 1,284 g of tetradecyl alcohol melted under heating, 20 g of tin tetrachloride as a catalyst was added, and then 148 g of epichlorohydrin was added to the mixture with stirring. After stirring the resulting mixture for 3 hours at 120° to 130° C., the reaction mixture was cooled to 45° C. and 50° C. and then a small amount of an aqueous solution of potassium carbonate was added under vigorous stirring to decompose the catalyst. Then, anhydrous sodium sulfate was added, and after drying, the mixture was filtrated and distilled under reduced pressure to separate the unreacted tetradecyl alcohol and the crude reaction product, which was further distilled to obtain 360 g of tetradecyl-3-chloro-2-hydroxypropyl ether having a boiling point of 176° to 180° C./3 mm Hg (yield 73.3%). Into a flask, 307 g of tetradecyl-3-chloro-2-hydroxypropyl ether and 237 g of pyridine were introduced and refluxed for 10 hours at 130° to 140° C. After cooling, the excess pyridine was distilled out under reduced pressure, and then the residue was recrystallized from a mixture (1:2 by volume) of acetone and ethanol to obtain 272 g of 2-hydroxy-3-tetradecyloxypropyl pyridinium chloride (yield 71.6%).

The thione compound which can be used in the present invention in combination with the bleach inhibitor represented by the general formula (I) or (II) is represented by the following general formula (III):

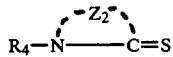  (III)

wherein $R_4$ represents an aliphatic group, for example, a substituted or unsubstituted alkyl group, an aryl group, for example, a substituted or unsubstituted aryl group, for example, a phenyl group, a naphthyl group, etc., or a heterocyclic group; $Z_2$ represents an atomic group necessary for forming a heterocyclic ring with the N-C moiety, where the carbon atom and the nitrogen atom of the N-C moiety which form the ring can be substituted. The heterocyclic ring can contain one or more additional hetero atoms, such as sulfur, selenium, oxygen, etc., in addition to nitrogen. Also, the heterocyclic ring containing $Z_2$ can be a 5-membered or 6-membered heterocyclic ring.

In the general formula (III), $Z_2$ represents an atomic group necessary for forming a heterocyclic group, for example, a thiazolidine-2-thione ring (such as a thiazolidine-2-thione ring, a 4-methylthiazolidine-2-thione ring, etc.), an imidazolidine-2-thione ring (such as a 1,3-dimethylimidazolidine-2-thione ring, a 1,3-diethylimidazoline-2-thione ring, etc.), a selenazolidine-2-thione ring (such as a selenazolidine-2-thione ring, a 4-methylselenazolidine-2-thione ring, etc.), a 1,3,4-thiadiazoline-2-thione ring (such as a 1,3,4-thiadiazoline-2-thione ring, a 5-methyl-1,3,4-thiadiazoline-2-thione ring, a 5-methyl-1,3,4-thiadiazoline-2-thione ring, a 5-ethylthio-1,3,4-thiadiazoline-2-thione ring, a 5-[2-(4-phenyl-5-thio-1,3,4-thiazolidin-2-yl)mercaptoethylthio]-1,3,4-thiadiazoline-2-thione ring, etc.), a 1,3,4-selenadiazoline-2-thione ring (such as a 1,3,4-selenadiazoline-2-thione ring, a 5-ethyl-1,3,4-selenadiazoline-2-thione ring, etc.), a 4-thiazoline-2-thione ring (such as a 4-methyl-4-thiazoline-2-thione ring, a 4-phenyl-4-thiazoline-2-thione ring, a 4-methyl-5-ethoxycarbonyl-4-thiazoline-2-thione ring, a 4,5-trimethylenethiazoline-2-thione ring, a 4,5-tetramethylenethiazoline-2-thione ring, etc.), a 4-selenazoline-2-thione ring (such as a 4-selenazoline-2-thione ring, a 4-methyl-4-selenazoline-2-thione ring, a 4-phenyl-4-selenazoline-2-thione ring, etc.), a 1,2-dihydropyridine-2-thione ring (such as a 1,2-dihydropyridine-2-thione ring, a 6-ethyl-1,2-dihydropyridine-2-thione ring, etc.), a benzothiazoline-2-thione ring (such as a benzothiazoline-2-thione ring, a 6-methylbenzothiazoline-2-thione ring, a 6-ethylbenzothiazoline-2-thione ring, a 6-methoxybenzothiazoline-2-thione ring, a 6-chlorobenzothiazoline-2-thione ring, a 5-methylbenzothiazoline-2-thione ring, etc.), a benzoxazoline-2-thione ring (such as a benzoxazoline-2-thione ring, a 6-ethylbenzoxazoline-2-thione ring, a 6-methoxybenzoxazoline-2-thione ring, a 5-methylbenzoxazoline-2-thione ring, etc.), a benzimidazoline-2-thione ring (such as a 1,3-dimethylbenzimidazoline-2-thione ring, a 1,3-di-n-propylbenzimidazoline-2-thione ring, a 1,3-di-n-decylbenzimidazoline-2-thione ring, a 1,3-dibenzylbenzimidazoline-2-thione ring, a 5-chloro-1,3-dimethylbenzimidazoline-2-thione ring, a 5-methyl-1,3-dibenzylbenzimidazoline-2-thione ring, etc.), a benzoselenazoline-2-thione ring (such as a benzoselenazoline-2-thione ring, a 6-ethylbenzoselenazoline-2-thione ring, a 6-methoxybenzoselenazoline-2-thione ring, a 6-chlorobenzoselenazoline-2-thione ring, etc.), a 1,2-dihydroquinoline-2-thione ring (such as a 1,2-dihydroquinoline-2-thione ring, a 6-methyl-1,2-dihydroquinoline-2-thione ring, a 6-chloro-1,2-dihydroquinoline-2-thione ring, etc.), and the like.

The aliphatic group for $R_4$ includes an unsubstituted alkyl group (for example, having 1 to 10 carbon atoms), an alkyl group substituted with a hydroxy group, an aryl group, e.g., phenyl, naphthyl, etc., a morpholino group, etc., such as a methyl group, an ethyl group, a propyl group, a hexyl group, a decyl group, a hydroxyethyl group, a benzyl group, a morpholinoethyl group and the like. The aryl group includes an unsubstituted aryl group or an aryl group substituted with an alkyl group (for example, having 1 to 4 carbon atoms), an alkoxy group (for example, having 1 to 4 carbon atoms), a halogen atoms, etc., such as a phenyl group, a 2-methylphenyl group, a 4-methoxyphenyl group, a 4-chlorophenyl group, and the like. The heterocyclic group includes, for example, a nitrogen containing heterocyclic ring such as a 6-membered nitrogen containing heterocyclic ring (for example, a 2-pyridyl group, etc.), and the like.

Preferred specific examples of the above-described compounds represented by the general formula (III) are those illustrated hereinafter.

| Compound (III-1) | 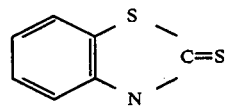 | Melting Point 90° C. |
|---|---|---|
| Compound (III-2) | 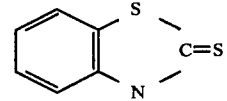 | Melting Point 76° C. |
| Compound (III-3) | 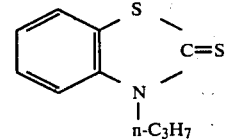 | Melting Point 74° C. |

-continued
| | | |
|---|---|---|
| Compound (III-4) | 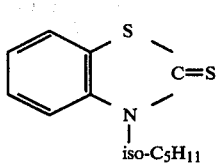 | Melting Point 55° C. |
| Compound (III-5) | 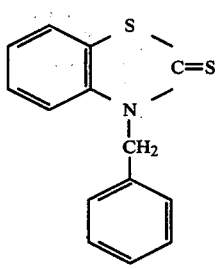 | Melting Point 149° C. |
| Compound (III-6) | 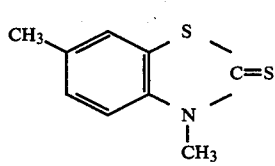 | Melting Point 190° C. |
| Compound (III-7) |  | Melting Point 87° C. |
| Compound (III-8) | 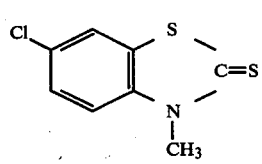 | Melting Point 130° C. |
| Compound (III-9) | 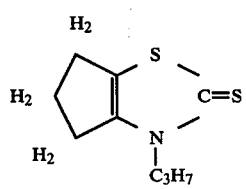 | Melting Point 81°–82° C. |
| Compound (III-10) | 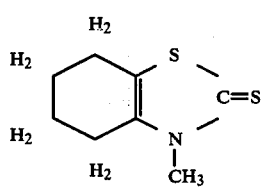 | Melting Point 102° C. |
| Compound (III-11) | 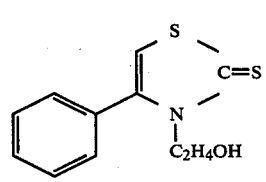 | Melting Point 96° C. |
| Compound (III-12) | 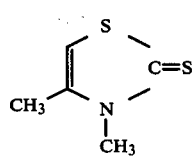 | Melting Point 114° C. |

-continued
| | | |
|---|---|---|
| Compound (III-13) | 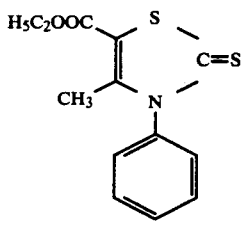 | Melting Point 162° C. |
| Compound (III-16) | 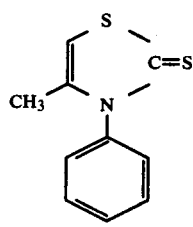 | Melting Point 82° C. |
| Compound (III-15) | 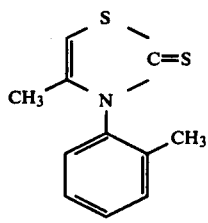 | Melting Point 119° C. |
| Compound (III-14) | 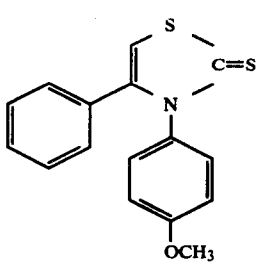 | Melting Point 166° C. |
| Compound (III-17) | 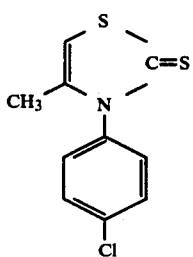 | Melting Point 113° C. |
| Compound (III-18) | 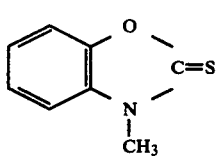 | Melting Point 133° C. |
| Compound (III-19) | 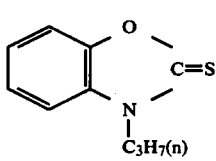 | Melting Point 92° C. |
| Compound (III-20) | 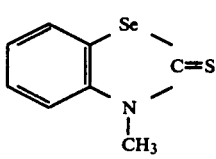 | Melting Point 80° C. |

-continued
| | | |
|---|---|---|
| Compound (III-21) | 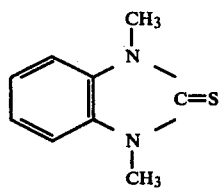 | Melting Point 151° C. |
| Compound (III-22) | 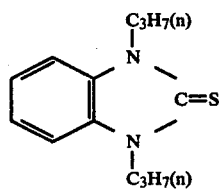 | Liquid |
| Compound (III-23) | 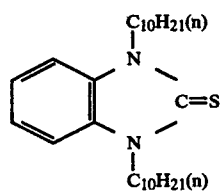 | Liquid |
| Compound (III-24) | 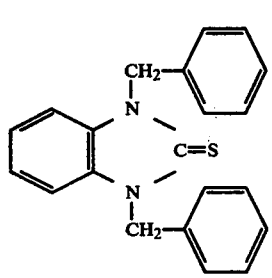 | Melting Point 191° C. |
| Compound (III-25) | 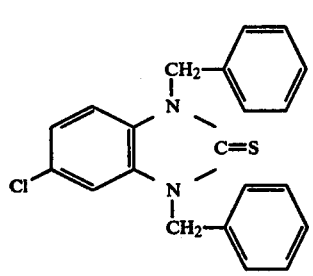 | Melting Point 169° C. |
| Compound (III-26) | 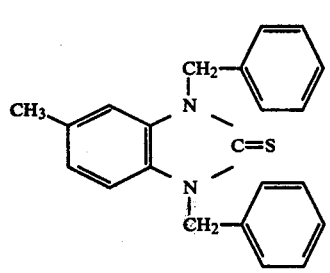 | Melting Point 143° C. |
| Compound (III-27) | 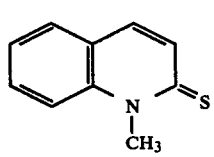 | Melting Point 118° C. |
| Compound (III-28) | 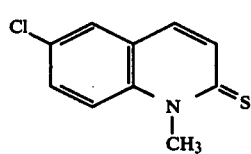 | Melting Point 184° C. |

-continued
| | | |
|---|---|---|
| Compound (III-29) | 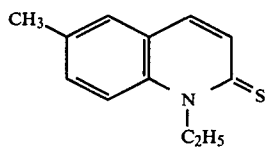 | Melting Point 94° C. |
| Compound (III-30) | 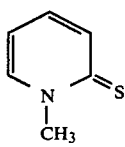 | Melting Point 90° C. |
| Compound (III-31) | 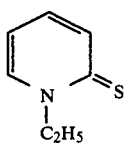 | Melting Point 46° C. |
| Compound (III-32) | 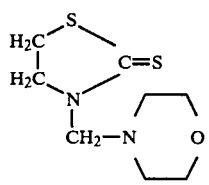 | Melting Point 123° C. |
| Compound (III-33) | 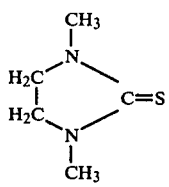 | Melting Point 62.5° C. |
| Compound (III-34) | 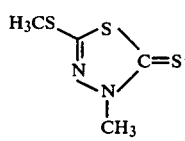 | Melting Point 88° C. |
| Compound (III-35) | 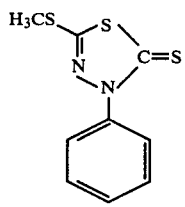 | Melting Point 108° C. |
| Compound (III-36) | 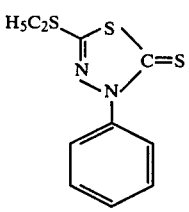 | Melting Point 66° C. |
| Compound (III-37) | 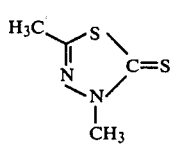 | Melting Point 152° C. |

| Compound (III-38) | 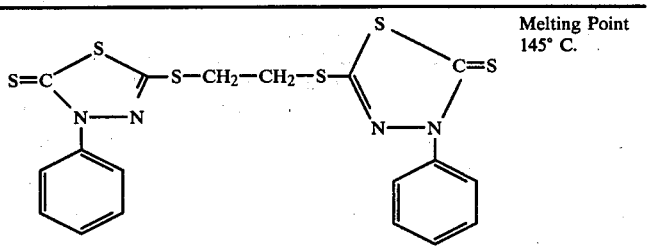 | Melting Point 145° C. |
|---|---|---|

The compounds which can be used in the present invention can be prepared by methods conventionally known. Specific synthesis examples of these compounds are shown below.

SYNTHESIS EXAMPLE 1 (COMPOUNDS III-1 TO III-8)

These compounds can be prepared by the method described in *Journal of the Chemical Society*, pages 473 to 476 (1939) using 2-mercaptobenzothiazole as a starting material.

SYNTHESIS EXAMPLE 2 (COMPOUNDS III-9 TO III-17)

These compounds can be prepared by the method described in *Journal of the Chemical Society*, pages 1503 to 1509 (1949) using a reaction between a salt of dithiocarbamic acid and an α-haloketone.

SYNTHESIS EXAMPLE 3 (COMPOUNDS III-18 AND III-19)

These compounds can be prepared by the method described in ibid., pages 143 to 151 (1939).

SYNTHESIS EXAMPLE 4 (COMPOUND III-20)

The compound can be prepared by the method described in ibid., pages 1762 to 1766 (1939).

SYNTHESIS EXAMPLE 5 (COMPOUND III-21)

This compound can be prepared by the method described in *Nippon Yakugaku Zasshi*, Vol. 74, pages 1365 to 1369 (1954).

SYNTHESIS EXAMPLE 6 (COMPOUNDS III-22)

2-Mercaptobenzimidazole and an equivalent number of moles of propyl iodide were heated and refluxed in ethanol for 6 hours to prepare 2-propylthiobenzimidazole which was then heated and refluxed with an equivalent number of moles of propyl iodide in dioxane for 12 hours. After distilling off dioxane, pyridine was added to the mixture and heated and refluxed for 1 hour. After removing pyridine under reduced pressure, the resulting yellow oily residue was passed through a silica gel column for chromatography using n-hexane as solvent to provide a colorless liquid.

Elemental Analysis: Calculated for $C_{13}H_{18}N_2S$ (%): C 66.64; H 7.74; H 11.96; Found (%): C 66.75; H 7.63; N 11.42.

SYNTHESIS EXAMPLE 7 (COMPOUNDS III-23 TO III-26)

These compounds can be prepared by a method similar to that in Synthesis Example 6 except for using corresponding starting materials.

SYNTHESIS EXAMPLE 8 (COMPOUNDS III-27 TO III-29)

These compounds can be prepared by the method described in *Berichte der Deutschen Chemischen Gesellschaft*, Vol. 33, page 3359, and ibid., Vol. 35, page 3682.

SYNTHESIS EXAMPLE 9 (COMPOUND III-30)

This compound can be prepared by the method described in *Justus Liebigs Annalen der Chemie*, Col. 331, page 245.

SYNTHESIS EXAMPLE 10 (COMPOUNDS III-31 AND III-33)

These compounds can be prepared by the method described in *Journal of Organic Chemistry*, Vol. 14, page 946.

SYNTHESIS EXAMPLE 11 (COMPOUND III-32)

6.5 g of thiazoline-2-thione and 4.5 ml of formalin (37%) were mixed at 50° C. and an ethanol solution containing 5 g of morpholine was gradually added thereto. The white crystals which formed were recrystallized from ethanol to provide crystals having a melting point of 123° C.

SYNTHESIS EXAMPLE 12 (COMPOUNDS III-34, III-36 AND III-38)

These compounds can be prepared by the method described in *Journal fur Praktische Chemie*, Vol. 60, page 53 and ibid., Vol. 60, pages 187 to 188.

SYNTHESIS EXAMPLE 13 (COMPOUND III-35)

This compound can be prepared by the method described in *Berichte der Deutschen Chemischen Gesellschaft*, Vol. 27, page 2513.

SYNTHESIS EXAMPLE 14 (COMPOUND III-37)

This compound can be prepared by the method described in *Chemical Abstracts*, Vol. 33, page 2518.

The compounds represented by the general formula (III) do not per se show any silver bleach inhibiting effect. However, when they are used together with a silver bleach inhibitor of the present invention, they exhibit a bleach inhibiting effect. Therefore, a high infrared density can be obtained with a small amount of coated silver in comparison with the case where a silver bleach inhibitor is used alone.

The amount of the silver bleach inhibitor used in the photographic light-sensitive material of the present invention can be varied over a wide range, depending on the characteristics of the silver bleach inhibitor and the silver halide emulsion employed, but generally it is about $1 \times 10^{-7}$ to about 10 g, preferably $1 \times 10^{-5}$ to 10 g, per mole of silver in the emulsion layer.

The amount of the thione compound used in the photographic light-sensitive material of the present invention can also be varied over a wide range, depending on the characteristics of the silver bleach inhibitor employed, the silver halide emulsion employed and the thione compound per se, but generally it is about $1\times10^{-5}$ to about $1\times10^{1}$ mole, preferably $1\times10^{-4}$ to $1\times10^{-1}$ mole, per mole of the silver bleach inhibitor employed.

The thione compound represented by the general formula (II) can be incorporated into a photographic emulsion in a number of ways, e.g., by dissolving it in an organic solvent which is miscible with water such as acetone, ethanol, etc., and has a boiling point of about 150° C. or less. Also, it can be dissolved together with a silver bleach inhibitor in a high boiling point organic solvent, e.g., having a boiling point of about 180° C. or more, for example, methylphthalate, ethylphthalate, n-butylphthalate, di-n-butylphthalate, dioctylphthalate, tricresyl phosphate, dioctylbutyl phosphate, acetyltributyl citrate, etc., or a low boiling point organic solvent having a boiling point of about 30° to about 150° C., for example, ethyl acetate, butyl acetate, butyl propionate, $\beta$-ethoxyethylacetate, etc., the solution dispersed in an appropriate photographic hydrophilic colloid and the resulting dispersion incorporated into a photographic emulsion. The high boiling point organic solvent and the low boiling point organic solvent described above can be used as a mixture thereof, if desired. Further, the thione compound can be solubilized in an aqueous solution of a surface active agent in a manner similar to the method described in U.S. Pat. No. 3,822,135 and then incorporated into a photographic emulsion.

Upon color development of the color photographic light-sensitive material of the present invention with a color developer solution containing a color developing agent, silver images necessary for sound images are formed together with the yellow, magenta and cyan dyes for color images. Of course, silver images are formed in the color image portions but they are easily bleached in a conventional bleaching bath or blixing bath. On the contrary, the silver images formed in the sound track forming layer are not bleached in a bleaching bath or blixing bath and remain therein. That is, since the sound images (silver images) can be obtained using only conventional color processing steps, the sound development steps for forming silver images as in conventional methods are unnecessary, and hence processing is simplified.

In other words, silver sound development is unnecessary using the color photographic light-sensitive material of the present invention. According to the present invention, a special processing step in which a viscous sound developer is selectively applied onto the sound track areas can be omitted. Further, since the silver images which are formed by color development are retained in the sound track areas and can be used as sound images, a rehalogenation of the developed silver is not necessary, and bleaching and fixing can be carried out in a single bath (a blix bath), whereby processing is simplified.

Furthermore, according to the present invention, the sound track images are composed of silver images and, therefore, the optical density is not reduced by light, heat and humidity, while sound track images composed of an organic dye having an absorption in the infrared region have the disadvantage that optical density is reduced on exposure to light, heat and humidity.

Moreover, where a conventional light-sensitive material has a yellow filter layer which contains yellow colloidal silver or an antihalation layer containing black colloidal silver, it cannot be sound development processed by conventional techniques because colloidal silver is rehalogenated during bleaching and is developed in the sound development step. On the contrary, the color photographic light-sensitive material of the present invention can contain colloidal silver because a sound development step is unnecessary in processing the same.

The hydrophilic colloids which can be used in the emulsion of the present invention are selected from those conventionally used in the photographic arts and include a protein such as gelatin, albumin, casein, etc., a cellulose derivative such as carboxymethyl cellulose, hydroxyethyl cellulose, etc., a saccharide derivative such as agar-agar, sodium alginate, a starch derivative, etc., a synthetic hydrophilic colloid such as polyvinyl alcohol, poly-N-vinyl pyrrolidone, a copolymer of acrylic acid, polyacrylamide or a derivative thereof, and the like. If desired, a compatible mixture of such colloids can also be used. Of these colloids, gelatin is most commonly used. It can be replaced partially or completely by a synthetic high molecular weight compound, that is, a gelatin derivative prepared by reacting or modifying the amino, imino, hydroxy or carboxy groups contained as functional groups in the gelatin molecule with a compound having a group capable of reacting with the above-described groups, or grafted gelatin such as those prepared by grafting other polymer chains onto a gelatin molecule.

The light-sensitive silver halide emulsion used in the present invention further comprises a conventional silver halide as is used in the photographic arts such as silver chloride, silver bromide, silver iodide, silver chlorobromide, silver iodobromide, silver chloroiodobromide or a mixture thereof suspended in the hydrophilic colloid as described above, and can be prepared according to conventional methods, for example, an ammonia process, a neutral process, an acid process, a single jet method, a double jet method, a controlled double jet method, etc., can be used. Mixtures of two or more silver halide emulsions which are separately prepared and thereafter mixed can also be used. Methods for the preparation of silver halide emulsions are described in C.E.K. Mees, *The Theory of the Photographic Process,* Macmillan Co., P. Glafkides, *Photographic Chemistry,* Fountain Press, etc. It is preferred that the particle size of the silver halide in the sound track layer be less than about $0.5\mu$, more preferably less than $0.2\mu$. The particle size of the silver halide in the picture image-forming layer of the light-sensitive material of the present invention is not particularly limited, and can be appropriately selected by one skilled in the art based on the desired end use of the material. The light-sensitive silver halide emulsions of the present invention can be subjected to a variety of conventional treatments and/or contain a variety of conventional additives as are well known in the photographic arts, some of which are exemplified below.

The light-sensitive silver halide emulsions of the present invention can be chemically sensitized with active gelatin or by the methods as described in U.S. Pat. Nos. 1,574,944, 1,623,499 and 2,410,689. The light-sensitive silver halide emulsions of the present invention can also be sensitized with a salt of a noble metal, such as palladium or gold as described in U.S. Pat. Nos. 2,448,060, 2,399,083 and 2,642,361. The light-sensitive silver halide emulsions of the present invention can further be spectrally sensitized with a cyanine dye or a merocyanine dye as described in U.S. Pat. Nos. 2,519,001, 2,666,761, 2,734,900, 2,739,964 and 3,481,742.

The light-sensitive silver halide emulsions of the present invention can be reduction-sensitized with a reducing agent such as a stannous salt as described in U.S. Pat. No. 2,487,850, and a polyamide as described in U.S. Pat. Nos. 2,518,698 and 2,521,929.

The light-sensitive silver halide emulsions of the present invention can be stabilized with an anti-fogging agent or a stabilizer. For such purpose, an azaindene, a mercaptotetrazole, a salt of a noble metal such as palladium or platinum, an oxime, an imidazolium salt, a tetrazolium salt, and the like can be used. These compounds are described, for example, in U.S. Pat. Nos. 2,444,605, 2,886,437, 2,403,927, 3,399,987, 2,597,915, 3,566,265, 2,694,716, 2,131,038, 2,518,698, 3,369,904, 2,419,974 and 2,419,975 and British Patent 623,448.

The hydrophilic colloid which can be used in the photographic material of the present invention can be hardened with a hardener such as an aldehyde hardener, a methylol hardener, a 1,4-dioxane hardener, an aziridine hardener, an isooxazole hardener, a carbodiimide hardener, an active halogen hardener, an active vinyl hardener, etc. Typical examples of these hardeners are described in U.S. Pat. Nos. 3,232,764, 3,288,775, 2,732,303, 3,635,718, 3,232,763, 2,732,316, 2,586,168, 3,103,437, 3,017,280, 2,983,611, 2,725,294, 2,725,295, 3,100,704, 3,091,537, 3,321,313 and 3,543,292 and British Patents Nos. 974,723, 1,167,207 and 994,869.

The photographic light-sensitive material of the present invention can contain a plasticizer such as glycerol or a coating aid such as saponin or those described in U.S. Pat. Nos. 3,415,649, 3,441,413, 3,502,473, 3,514,293, 3,506,449, 3,539,352, 3,545,974, 3,507,660, 3,442,654, 3,475,174, 3,462,520, 3,493,379, 3,516,883, 3,516,835, 3,589,906, 3,617,292, 3,619,199 and 3,663,229.

The photographic light-sensitive material of the present invention can contain an antistatic agent, if desired, as described in, for example, U.S. Pat. Nos. 3,428,456, 3,437,484, 3,457,076, 3,549,375, 3,549,369, 3,551,152, 3,552,972, 3,547,643, 3,564,043, 3,615,531, 3,625,695, 3,655,387, 3,653,906, 3,655,386, 3,686,368, 3,756,828 and 3,754,924.

The photographic light-sensitive material of the present invention can contain, as a filter dye or an irradiation preventing dye, compounds as are described, for example, in U.S. Pat. Nos. 2,274,782, 2,525,583, 2,956,879, 3,177,078 and 3,252,921 and Japanese Patent No. 22069/64. The dye can be mordanted, for example, by the method described in U.S. Pat. No. 3,282,699, if desired.

The photographic light-sensitive material of the present invention can contain, as an ultraviolet absorbing agent, the compounds as described, for example, in U.S. Pat. Nos. 2,415,624, 3,052,636, 3,074,971, 3,085,097, 3,067,456, 3,215,536, 2,719,086, 2,537,866, 2,784,087, 2,882,150, 2,875,053, 2,739,971, 3,097,100, 3,060,029, 2,632,701, 2,888,346 and 2,748,021.

The photographic light-sensitive material of the present invention can contain, as a fluorescent whitening agent, the compounds as described, for example, in U.S. Pat. Nos. 3,630,738, 3,615,544, 3,586,673 and 3,434,837 and British Pat. Nos. 1,332,475, 1,319,763 and 1,333,586.

In the photographic light-sensitive material of the present invention, all open-chain ketomethylene yellow dye-forming couplers can be advantageously used. Typical examples are benzoyl acetanilide type couplers and pivaloyl acetanilide couplers. All magenta dye-forming couplers such as pyrazolone type couplers and indazolone type couplers can be advantageously used. All cyan dye-forming couplers such as phenol type couplers and naphthol type couplers can be advantageously used. Such materials, their characteristics and functions are well known in the art. These couplers can have a coupling-off group on the active carbon atom of the coupling position thereof, if desired. The color couplers employed preferably have a ballast group in the molecule, whereby the couplers become non-diffusible. The terms "coupling-off group", "ballast group" and "diffusion resistant" have been widely used with respect to color couplers and hence they are well known and easily understood by one skilled in the art.

In order to render the coupler diffusion resistant, a hydrophobic group having at least 8 carbon atoms, such as an alkyl group or an alkylaryl group, is conventionally introduced into the coupler molecule. Many such hydrophobic ballast groups are well known, and can be used in the present invention.

The ballast group can be bonded to the coupler nucleus directly or through an amino bond, an ether bond, a thioether bond, a carbonamide bond, a sulfonamide bond, a ureido bond, an ester bond, an imido bond, a carbonyl bond, a sulfonyl bond, etc., as is well known in the art.

Typical examples of ballast groups are illustrated below.

(i) Alkyl groups and alkenyl groups such as

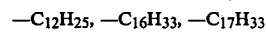

(ii) Alkoxyalkyl groups such as

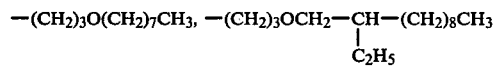

(iii) Alkylaryl groups such as

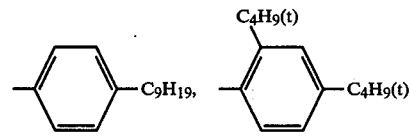

(iv) Alkylaryloxyalkyl groups such as

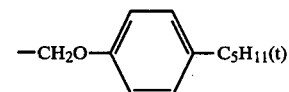

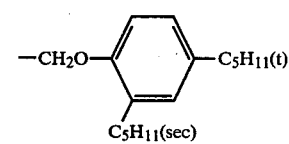

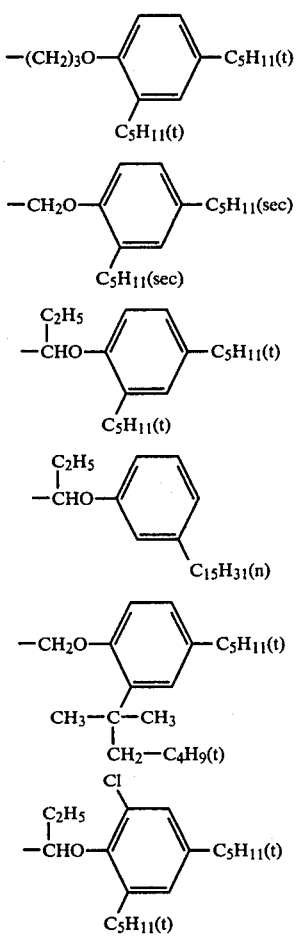

(v) Acylamidoalkyl groups such as

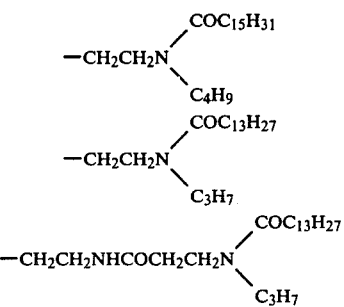

as described in U.S. Pat. Nos. 3,337,344 and 3,418,129.

(vi) Alkoxyaryl groups and aryloxyaryl groups such as

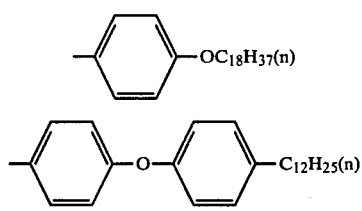

(vii) Residues having both a carboxy or sulfo group and a long chain aliphatic group such as an alkyl or alkenyl group, such as

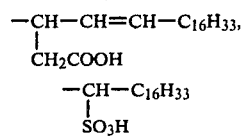

(viii) Alkyl groups substituted with an ester group such as

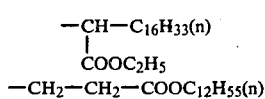

(ix) Alkyl groups substituted with an aryl group or a heterocyclic groups such as

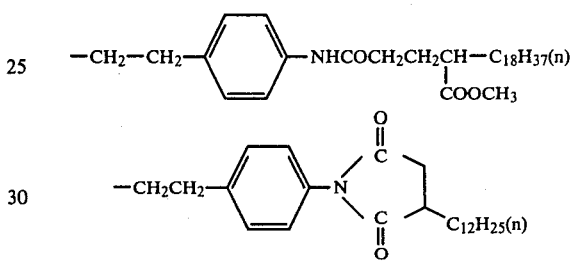

(x) Aryl groups substituted with an aryloxyalkoxycarbonyl group such as

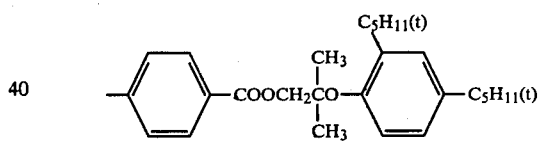

Typical diffusion resistant couplers which can be used in the present invention are described in detail hereinafter.

As yellow couplers, an open-chain diketomethylene type compound is generally used. Examples of these couplers are described, for example, in U.S. Pat. Nos. 3,341,331, 2,875,057 and 3,551,155, German Patent Application (OLS) No. 1,547,868, U.S. Pat. Nos. 3,265,506, 3,582,322 and 3,725,072, German Patent Application (OLS) No. 2,162,899, U.S. Pat. Nos. 3,369,895 and 3,408,194 and German Patent Application (OLS) Nos. 2,057,941, 2,213,461, 2,219,917, 2,261,361 and 2,263,875.

As magenta couplers, a 5-pyrazolone type compound is widely used, but an indazolone type compound and a cyano-acetyl compound are also used. Examples of these couplers are described, for example, in U.S. Pat. Nos. 2,439,098, 2,600,788, 3,062,653 and 3,558,319, British Pat. No. 956,261, U.S. Pat. No. 3,582,322, 3,615,506, 3,519,429, 3,311,476, 3,419,391 and 3,935,015, British Pat. Nos. 1,470,552, 1,464,361, German Pat. No. 1,810,464, Japanese Patent Publication No. 2016/69 and U.S. Pat. No. 2,983,608.

As cyan couplers, a phenol derivative or a naphthol derivative is widely used. Examples of these couplers are described, for example, in U.S. Pat. Nos. 2,369,929, 2,474,293, 2,698,794, 2,895,826, 3,311,476, 3,458,315, 3,560,212, 3,582,322, 3,591,383, 3,386,301, 2,434,272, 2,706,684, 3,034,892, 3,770,436, 3,933,508 and 3,583,971 and British Pat. No. 1,201,110.

Further, DIR couplers which are capable of releasing a compound inhibiting development during color development or other compounds capable of releasing a compound inhibiting development can also be used. Examples of these compounds are described, for example, in U.S. Pat. Nos. 3,148,062, 3,227,554, 3,253,924, 3,617,291, 3,622,328 and 3,705,201, British Pat. No. 1,201,110, and 1,450,479 and U.S. Pat. Nos. 3,297,445, 3,379,529, 3,639,417 and 3,930,863.

Two or more of the above-described couplers and/or compounds can be incorporated in the same layer or the same couplers and/or compounds can be present in two or more layers of the photographic material in order to fulfill the characteristics required in the photographic light-sensitive material.

The couplers and other additives can be incorporated into a hydrophilic colloid of the photographic material in a conventional manner. One method for incorporation is described, for example, in U.S. Pat. No. 2,322,027. In general, the coupler is dissolved in a high boiling point organic solvent having a boiling point of about 180° C. or more, for example, an alkyl ester of phthalic acid such as methyl phthalate, ethyl phthalate, propyl phthalate, n-butyl phthalate, di-n-butyl phthalate, n-amyl phthalate, isoamyl phthalate and dioctyl phthalate, an alkylamide such as N,N-diethyllaurylamide, a trimellitate ester such as tri-tert-octyl trimellitate, a phosphoric acid ester such as triphenyl phosphate, tricresyl phosphate and dioctylbutyl phosphate, a citric acid ester such as acetyltributyl citrate and the like, or a low boiling point organic solvent having a boiling point of about 30° to 150° C., for example, a lower alkyl ester of acetic acid such as ethyl acetate and butyl acetate, ethyl propionate, sec-butyl alcohol, methyl isobutyl ketone, β-ethoxyethyl acetate, methyl cellosolve acetate and the like, and then dispersed in the desired photographic hydrophilic colloid as earlier exemplified. The high boiling point organic solvent and the low boiling point organic solvent can be used in admixture, if necessary.

A coupler which has an acid group such as a carboxylic acid group of a sulfonic acid group is generally introduced into a hydrophilic colloid as an aqueous alkaline solution.

A coupler is generally used in an amount of about $2 \times 10^{-3}$ to about $5 \times 10^{-1}$ mole, preferably $1 \times 10^{-2}$ to $5 \times 10^{-1}$ mole, per mole of silver in the emulsion layer.

The photographic support on which a coating solution for forming a hydrophilic colloidal photographic layer is applied according to the present invention can be a conventional support as is used for a photographic light-sensitive material, and is preferably flexible, such as a cellulose nitrate film, a cellulose acetate film, a cellulose acetate butyrate film, a cellulose acetate propionate film, a polystyrene film, a polyethylene terephthalate film, a polycarbonate film, a laminate of these polymers, and the like. When the adhesion between a support and a photographic emulsion layer is unsatisfactory, a subbing layer which adheres to both of them can be provided on the support. The surface of the support can also be pre-treated by corona discharge, an ultraviolet radiation treatment, a flame treatment and the like, in order to further improve adhesiveness.

The color photographic light-sensitive material of the present invention is, after exposure, subjected to a conventional color processing to form dye images. The color processing basically includes a color development step, a bleaching step and a fixing step. Each step can be carried out individually, or two or more steps can be combined in one step where a processing solution having these two or more functions is used. One example of such combined bath is a blix bath. Also, each step can be divided into two or more sub-steps. For example, a process comprising a color development step, a first fixing step and a blixing step can be used. The color processing can further include a prehardening, a neutralization, a first development (black-and-white development), a stabilizing, a washing, and the like, if desired.

The temperature of processing can be varied depending on the photographic light-sensitive material, the color processing method and the like. In general, temperatures of 18° C. or more are used, although temperatures below 18° C. can be used. A temperature of 20° to 60° C., recently 30° to 60° C., is often conventionally used. Each step need not necessarily be at the same temperature.

A color developer solution is an alkaline solution having a pH value of more than about 8, preferably from 9 to 12, and contains, as a developing agent, a compound whose oxidation product is capable of forming a colored compound when reacted with a color forming agent, i.e., a color coupler.

The developing agents described above include compounds capable of developing exposed silver halide and having a primary amino group on an aromatic ring, and precursors which can form such compounds. Preferred typical examples of such developing agents are, for example, 4-amino-N,N-diethylaniline, 3-methyl-4-amino-N,N-diethylaniline, 4-amino-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline, and the salts thereof (for example, the sulfates, the hydrochlorides, the sulfites, the p-toluene sulfonates and the like). Other developing agents such as those described in U.S. Pat. Nos. 2,193,015, 2,592,364 and 3,816,134, and L. F. A. Mason, *Photographic Processing Chemistry*, pages 226 to 229, Focal Press, London (1966) and 3-pyrazolidones can also be used together with these developing agents.

The color developer solution optionally can contain various additives. Typical examples of such additives include alkaline agents (for example, hydroxides, carbonates or phosphates of alkali metals or ammoniums); pH-adjusting agents or buffers (for example, weak acids such as acetic acid, boric acid, etc., weak bases, or salts thereof); developing accelerators (for example, various pyridinium compounds or cationic compounds such as those described in U.S. Pat. Nos. 2,648,604 and 3,671,247; potassium nitrate; sodium nitrate; condensation products of polyethylene glycol and derivatives thereof such as those described in U.S. Pat. Nos. 2,533,990, 2,577,127 and 2,950,970; nonionic compounds such as polythioethers represented by those described in British Pat. Nos. 1,020,033 and 1,020,032; polymeric compounds having sulfite ester groups such as those described in U.S. Pat. No. 3,068,097; organic amines such as pyridine and ethanolamine; benzyl alcohol; hydrazines and the like); anti-fogging agents (for example, alkali metal bromides, alkali metal iodides, nitrobenzimidazoles such as those described in U.S. Pat. Nos. 2,496,940 and 2,656,271, mercaptobenzimidazole, 5-methyl-benzotriazole, 1-phenyl-5-mercaptotetrazole, compounds for use in rapid processing solutions such as those described in U.S. Pat. Nos. 3,113,864, 3,342,596, 3,295,976, 3,615,522 and 3,597,199, thiosulfonyl compounds such as those described in British Pat. No. 972,211, phenazine-N-oxides such as those described in Japanese Patent No. 41675/71, fogging inhibitors such as those described in *Kagaku Shashin Binran (Manual of Photographic Science)*, Vol. II, pages 29 to 47, and the like); stain or sludge preventing agents such as those described in U.S. Pat. Nos. 3,161,513 and 3,161,514 and British Pat. Nos. 1,030,442, 1,144,481 and 1,251,558; inter-image effect accelerators as described in U.S. Pat. No. 3,536,487; preservatives (for example, sulfites, bisulfites, hydroxylamine hydrochlorides, formaldehyde-bisulfite adducts, alkanolaminebisulfite adducts, etc.) and the like.

All bleaching solutions which contain a conventional bleaching agent such as potassium ferricyanide, bichromate, iron (III), etc., can be used. All oxidizing agents for silver used in conventional belaching solutions can be used in the bleaching bath of the present invention. Examples of these oxidizing agents are a water-soluble ferricyanide such as sodium ferricyanide, potassium ferricyanide, ammonium ferricyanide, etc., a water-soluble quinone such as quinone, chloroquinone, methylquinone, etc., a water-soluble ferric salt such as ferric chloride, ferric sulfate, ferric thiocyanate, ferric oxalate, etc., a water-soluble cupric salt such as cupric chloride, cupric nitrate, etc., a water-soluble cobalt salt such as cobalt chloride, ammonium cobalt nitrate, etc. Further, an alkali metal complex salt of a water-soluble organic acid with a polyvalent cation can preferably be used as the oxidizing agent. Typical examples of such organic acids are malonic acid, tartaric acid, ethyl malonic acid, malic acid, fumaric acid, diglycollic acid, thioglycollic acid, ethyliminodipropionic acid, nitrilotriacetic acid, ethylenediaminetetraacetic acid, aminotriacetic acid, ethylenedithioglycollic acid, dithioglycollic acid, etc.

The polyvalent cation used includes a ferric ion, a cobalt ion and a cupric ion. Sodium iron (III)-ethylenediaminetetraacetate complex salt is particularly preferred as the bleaching agent. Specific examples of bleaching solutions are described, for example, in *Journal of the Society of Motion Picture and Television Engineers*, Vol. 61, pages 667 to 701 (1953), U.S. Pat. No. 3,189,452, German Pat. Nos. 866,605 and 966,410, U.S. Pat. No. 3,582,322 and *British Journal of Photography*, Vol. 107, pages 122 to 123 and 126 (1966).

A fixing solution can be used in order to remove solubilized silver salt from the photographic material. All fixing solutions which contain a conventional solvent for silver halide can be used in the fixing solution of the present invention. For example, a water-soluble thiosulfate such as sodium thiosulfate, potassium thiosulfate, ammonium thiosulfate, etc., a water-soluble thiocyanate such as sodium thiocyanate, potassium thiocyanate, ammonium thiocyanate, etc., a water-soluble organic diol fixing agent containing an oxygen atom or a sulfur atom such as 3-thia-1,5-pentanediol, 3,6-dithia-1,8-octanediol, 9-oxa-3,6,12,15-tetrathia-1,17-heptadecanediol, etc., a water-soluble sulfur containing organic dibasic acid and a water-soluble salt thereof such as ethylenebisthioglycollic acid and the sodium salt thereof, etc., an imidazolidinethione such as methylimidazolidinethione, etc., are preferably used. Further, the fixing agents described in L. F. A. Mason, *Photographic Processing Chemistry*, pages 187 to 188, Focal Press (1966) are also preferably used.

The bleaching step and the fixing step can be carried out in a single bath, if desired. Suitable combinations of a bleaching agent and a fixing agent as described above can be used. Specific examples of the fixing baths are described, for example, in German Pat. No. 866,605, U.S. Pat. No. 3,582,322, etc.

Each processing solution is advantageously used in circulation and regenerated. Such a method is described, for example, in *Journal of the Society of Motion Picture and Television Engineers*, Vol. 81, pages 293 to 295 (1972).

From the fixing solution silver is advantageously recovered. One silver recovery method is described, for example, in *Journal of the Society of Motion Picture and Television Engineers*, Vol. 81, pages 603 to 608.

The present invention will now be explained in greater detail by reference to the following examples. In the examples, the silver halide used in the sound track layer had a particle size of 0.2μ.

EXAMPLE 1

A silver chlorobromide emulsion (silver bromide: 30 mole%, silver content: 0.05 mole per 100 g of the emulsion) containing 0.1 g of 4-hydroxy-6-methyl-1,3,3a,7-tetrazaindene, 0.1 g of 2-hydroxy-4,6-dichloro-s-triazine sodium salt, a silver bleach inhibitor II-6, or I-2 as described below and the thione compound III-3 or III-24 of the present invention described above in an amount as indicated in Table 1 below was coated on a subbed cellulose triacetate film to prepare Samples (III), (IV), (V), (VI), (VII), (VIII), (IX), or (X). As control samples, the same emulsion containing neither a silver bleach inhibitor nor the thione compound was coated to prepare Samples (I) and (II).

Silver Bleach Inhibitor II-6

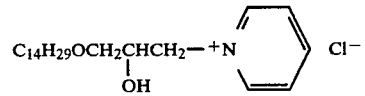

Silver Bleach Inhibitor I-2

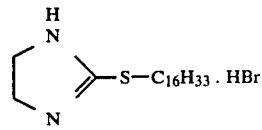

Samples (I) to (X) were exposed through a silver step wedge to a tungsten lamp having a color temperature of 2854° K. for 1/100 second, and then processed using Processing A or Processing B later described. The density in the infrared region of the thus-obtained film was measured through a Status S-58 filter using a Macbeth TD-206A type densitometer. The results obtained are shown in Table 1 below.

| Processing A | | |
|---|---|---|
| Processing Step | Temperature | Time |
| Prebath | 27° C. | 10 sec |
| Washing | " | 15 sec |
| Color Development | " | 5 min 20 sec |
| Washing | " | 15 sec |
| First Fixing | " | 1 min |
| Washing | " | 40 sec |
| Bleaching | " | 3 min |
| Washing | " | 1 min |
| Sound Development | room temperature | 15 sec |
| Washing | 27° C. | 15 sec |
| Second Fixing | " | 2 min |
| Washing | " | 5 min |
| Stabilizing | " | 10 sec |

The composition of each of the processing solutions was as follows:

Prebath Solution
| | |
|---|---|
| Water | 800 ml |
| Sodium Carbonate (monohydrate) | 10.0 g |
| Sodium Sulfate (anhydrous) | 50.0 g |
| Water to make | 1.0 l |

Color Developer Solution
| | |
|---|---|
| Water | 800 ml |
| Sodium Hexametaphosphate | 2.0 g |
| Sodium Sulfite (anhydrous) | 4.0 g |
| 2-Amino-5-diethylaminotoluene Hydrochloride | 3.0 g |
| Sodium Carbonate (monohydrate) | 25.0 g |
| Potassium Bromide | 2.0 g |
| Water to make | 1.0 l |

First Fixing Solution and Second Fixing Solution
| | |
|---|---|
| Water | 600 ml |
| Sodium Thiosulfate (pentahydrate) | 240 g |
| Sodium Sulfite (anhydrous) | 15.0 g |
| Glacial Acetic Acid | 12.0 g |
| Boric Acid | 6.0 g |
| Potassium Alum | 15.0 g |
| Water to make | 1.0 l |

Bleaching Solution
| | |
|---|---|
| Water | 800 ml |
| Potassium Bromide | 20.0 g |
| Potassium Bichromate | 5.0 g |
| Potassium Alum | 40.0 g |
| Sodium Acetate (trihydrate) | 3.0 g |
| Glacial Acetic Acid | 10.0 g |
| Water to make | 1.0 l |

Sound Developer Solution
(Solution A)
| | |
|---|---|
| Water | 600 ml |
| Sodium Sulfite (anhydrous) | 40.0 g |
| N-Methyl-p-aminophenol Sulfate | 40.0 g |
| Sodium Hydroxide | 40.0 g |
| Hydroquinone | 40.0 g |

(Solution B)
| | |
|---|---|
| Water | 300 ml |
| Tragacanth Gum | 5.0 g |
| Denatured Alcohol | 10 ml |

(Solution C)
| | |
|---|---|
| Ethylenediamine (70%) | 20 ml |

Solution A and Solution B were mixed, and, immediately before use, Solution C was added thereto with water to make 1.0 liter.

Stabilizing Bath
| | |
|---|---|
| Water | 800 ml |
| Formalin (37%) | 10 ml |
| Polyethylene Glycol (40% aq. soln.; molecular weight: 400) | 5 ml |
| Water to make | 1.0 l |

| Processing B | | |
|---|---|---|
| Processing Step | Temperature | Time |
| Prebath | 27° C. | 10 sec |
| Washing | " | 15 sec |
| Color Development | " | 5 min 20 sec |
| Washing | " | 15 sec |
| First Fixing | " | 1 min |
| Washing | " | 40 sec |
| Bleaching | " | 3 min |
| Washing | " | 1 min |
| Second Fixing | " | 2 min |
| Washing | " | 5 min |
| Stabilizing | " | 10 sec |

Each processing solution was same as that of Processing A.

TABLE 1

| | Sample | | | | | | | | | |
|---|---|---|---|---|---|---|---|---|---|---|
| | I | II | III | IV | V | VI | VII | VIII | IX | X |
| Silver Bleach Inhibitor | none | none | none | none | A | A | A | B | B | B |
| Amount Added (g/mole silver) | — | — | — | — | 8.5 | 8.5 | 8.5 | 1.7 | 1.7 | 1.7 |
| Thione Compound | — | — | 3 | 24 | — | 3 | 24 | — | 3 | 24 |
| Amount Added (g/mole silver) | — | — | 0.7 | 0.7 | — | 0.7 | 0.7 | — | 0.7 | 0.7 |
| Processing | A | B | B | B | B | B | B | B | B | B |
| Infrared Density | 1.05 | 0.04 | 0.07 | 0.04 | 1.55 | 1.90 | 1.80 | 1.60 | 1.95 | 1.80 |

As is shown in Table 1, a photographic material containing a silver bleach inhibitor and the thione compound according to the present invention gives a high density in the infrared region using conventional color processing. Particularly, Samples (VI), (VII), (IX) and (X) give very high density in the infrared region. On the other hand, a conventional photographic material containing no silver bleach inhibitor does not provide sufficiently high density in the infrared region unless it is processed with a sound development step.

EXAMPLE 2

An antihalation layer containing carbon black and a subbing layer were respectively coated on the opposite surfaces of a cellulose triacetate film support. On the subbing layer, the layers described below were coated in the recited order from the support to prepare a multilayer color photographic silver halide light-sensitive material.

| | |
|---|---|
| First Layer | Blue-Sensitive Layer |
| Second Layer | Intermediate Layer (1) |
| Third Layer | Red-Sensitive Layer |
| Fourth Layer | Intermediate Layer (2) |
| Fifth Layer | Green-Sensitive Layer |
| Sixth Layer | Protective Layer |

The couplers having the structure set forth below was dissolved in a conventional solvent mixture of dibutyl phthalate and ethyl acetate, dispersed in gelatin and incorporated into each of the blue-sensitive, red-sensitive and green-sensitive emulsion layers, respectively.

Yellow Dye-Forming Coupler

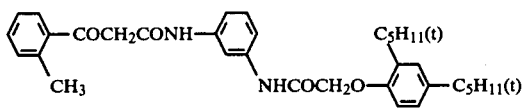

Cyan Dye-Forming Coupler

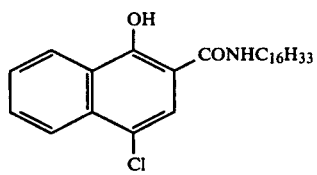

Magenta Dye-Forming Coupler

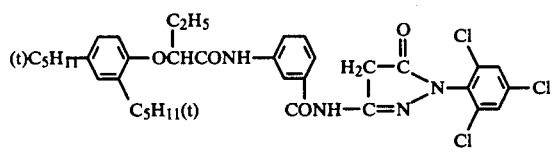

The structures of the spectral sensitizing dye used in the red-sensitive layer and the spectral sensitizing dye used in the green-sensitive layer and the amount thereof per mole of silver in the layer were as follows.

Spectral Sensitizing Dye for Red-Sensitive Layer

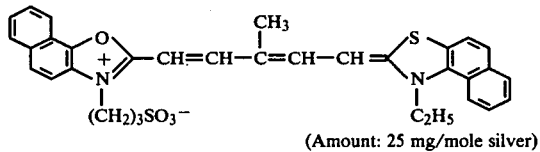

(Amount: 25 mg/mole silver)

Spectral Sensitizing Dye for Green-Sensitive Layer

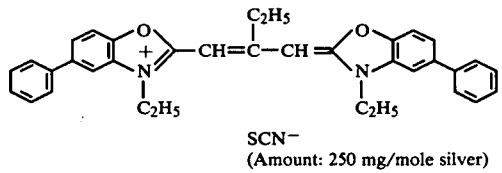

SCN⁻
(Amount: 250 mg/mole silver)

The coating amounts of silver, coupler and gelatin in each layer were as follows.

TABLE 2

| | Silver | Coupler | Gelatin |
|---|---|---|---|
| First Layer (Blue-Sensitive Layer) | 1.2 g/m² | 1.2 g/m² | 3.0 g/m² |
| Second Layer (Intermediate Layer) | — | — | 0.8 g/m² |
| Third Layer (Red-Sensitive Layer) | 0.8 g/m² | 1.5 g/m² | 1.8 g/m² |
| Fourth Layer (Intermediate Layer) | — | — | 0.8 g/m² |
| Fifth Layer (Green-Sensitive Layer) | 1.1 g/m² | 1.5 g/m² | 3.0 g/m² |
| Sixth Layer | — | — | 0.7 g/m² |

TABLE 2-continued

| | Silver | Coupler | Gelatin |
|---|---|---|---|
| (Protective Layer) | | | |

For the sixth layer (protective layer), a coating solution prepared by dispersing liquid paraffin in an aqueous gelatin solution was coated.

Sample (XI) thus prepared was used as a control. Further, color photographic light-sensitive materials according to the present invention were prepared in the following manner, that is, Samples (XII) to (XVII) were prepared by applying, between the fourth layer (Intermediate Layer (2)) and the green-sensitive layer, a sound track forming layer containing a silver bleach inhibitor and the thione compound of the present invention and an Intermediate Layer (3), in this order.

The coating amounts of silver, gelatin, a silver bleach inhibitor and the thione compound of the present invention in the sound track forming layer of Samples (XII) to (XVII) were as shown in Table 3.

TABLE 3

| | Sample | | | | | | |
|---|---|---|---|---|---|---|---|
| | XI | XII | XIII | XIV | XV | XVI | XVII |
| Silver (g/m²) | — | 1.5 | 1.5 | 1.2 | 1.5 | 1.5 | 1.2 |
| Gelatin (g/m²) | — | 2.0 | 2.0 | 1.6 | 2.0 | 2.0 | 1.6 |
| Silver Bleach Inhibitor | — | II-6 | II-6 | II-6 | I-2 | I-2 | I-2 |
| Amount Added (g/mole silver) | — | 8.5 | 8.5 | 8.5 | 6.0 | 6.0 | 6.0 |
| Thione Compound | — | — | III-3 | III-3 | — | III-3 | III-3 |
| Amount Added (g/mole silver) | — | — | 0.7 | 0.7 | — | 0.7 | 0.7 |

Samples (XI) to (XVII) were exposed in the same manner as described in Example 1 and were processed using Process B. The densities in the infrared region of the thusobtained films were measured in the same manner as described in Example 1. The results are shown in Table 4.

TABLE 4

| | Sample | | | | | | |
|---|---|---|---|---|---|---|---|
| | XI | XII | XIII | XIV | XV | XVI | XVII |
| Infrared Density | 0.35 | 1.66 | 1.95 | 1.60 | 1.80 | 2.04 | 1.80 |

As is shown in Table 4, a conventional photographic material containing no silver bleach inhibitor gives a low density in the infrared region unless it is processed with a sound development step. A photographic material containing both a silver bleach inhibitor and the thione compound according to the present invention provides a high density in the infrared region using a small amount of coated silver, in comparison with a photographic material containing only a silver bleach inhibitor.

EXAMPLE 3

On a subbed cellulose triacetate film, a silver chlorobromide emulsion (silver bromide: 30 mole%, silver content: 0.05 mole per 100 g of the emulsion) containing 0.1 g of 4-hydroxy-6-methyl-1,3,3a,7-tetrazaindene, 0.1 g of 2-hydroxy-4,6-dichloro-s-triazine sodium salt, a silver bleach inhibitor and the thione compound in an amount as indicated in Table 5 below using the method described below was coated to prepare Samples (XVIII), (XIX), (XX), (XXI), (XXII) and (XXIII).

Sample (XVIII): 8.5 ml of a 5% by weight aqueous solution of silver bleach inhibitor II-6 was added to 100 g of the emulsion.
Sample (XIX): 8.5 ml of a 1% by weight methanol solution of silver bleach inhibitor I-2 was added to 100 g of the emulsion.
Sample (XX): 0.085 g of silver bleach inhibitor I-2 was solubilized in 8.5 ml of a 5% by weight aqueous solution of silver bleach inhibitor II-6 and then added to 100 g of the emulsion.
Sample (XXI): 0.085 g of silver bleach inhibitor I-2 and 0.0085 g of thione compound (III-24) were solubilized in 8.5 ml of a 5% by weight aqueous solution of silver bleach inhibitor II-6 and then added to 100 g of the emulsion.
Sample (XXII): 1 g of silver bleach inhibitor I-2 was dissolved in 5 ml of tricresyl phosphate and dispersed in 100 g of a 10% by weight aqueous gelatin solution. 50 g of the dispersion thus-prepared was added to 100 g of the emulsion.
Sample (XXIII): 1 g of silver bleach inhibitor I-2 and 0.1 g of thione compound (III-24) were dissolved in 5 ml of a 10% by weight aqueous gelatin solution. 50 g of the dispersion thus-prepared was added to 100 g of the emulsion.

TABLE 5

| | Sample | | | | | |
|---|---|---|---|---|---|---|
| | XVIII | XIX | XX | XXI | XXII | XXIII |
| Silver (g/m$^2$) | 1.5 | 1.5 | 1.2 | 1.2 | 1.2 | 1.2 |
| Gelatin (g/m$^2$) | 2.0 | 2.0 | 1.6 | 1.6 | 1.6 | 1.6 |
| Silver Bleach Inhibitor II-6 (g/mole silver) | 8.5 | — | 8.5 | 8.5 | — | — |
| Silver Bleach Inhibitor I-2 | — | 1.7 | 1.7 | 1.7 | 7.4 | 7.4 |
| Thione Compound (III-24) (g/mole silver) | — | — | — | 0.17 | — | 0.74 |

Samples (XVIII) to (XXIII) were exposed in the same manner as described in Example 1 and were processed using the following Processing C or Processing D. The density in the infrared region of the thus-obtained films were measured in the same manner as described in Example 1. The results obtained are shown in Table 6.

TABLE 6

| | Sample | | | | | |
|---|---|---|---|---|---|---|
| | XVIII | XIX | XX | XXI | XXII | XXIII |
| Infrared Density Processing C | 1.41 | 1.20 | 1.55 | 1.87 | 1.50 | 1.90 |
| Infrared Density Processing D | 1.83 | 1.77 | 1.92 | 2.10 | 1.80 | 1.95 |

Processing C

| Processing Step | Temperature (°C.) | Time |
|---|---|---|
| Prebath | 27 | 15 sec |
| Washing | " | 2 sec |
| Color Development | 36.1 | 3 min |
| Washing | 27 | 40 sec |
| First Fixing | " | 40 sec |
| Washing | " | 40 sec |
| Bleaching | " | 1 min |
| Washing | " | 40 sec |
| Second Fixing | " | 40 sec |
| Washing | " | 1 min |
| Stabilizing | " | 15 sec |

The composition of the bleaching bath is set forth below, and the other processing solutions were the same as those of Processing A described hereinbefore.

| Bleaching Bath | |
|---|---|
| Water | 800 ml |
| Potassium Ferricyanide | 25 g |
| Potassium Bromide | 20 g |
| Water to make | 1 l |

Processing D

| Processing Step | Temperature (°C.) | Time |
|---|---|---|
| Prebath | 27 | 15 sec |
| Washing | " | 2 sec |
| Color Development | 36.1 | 3 min |
| Washing | 27 | 40 sec |
| Blixing | " | 1 min |
| Washing | " | 1 min |
| Stabilizing | " | 15 sec |

The composition of the blixing bath employed in Processing D was as follows:

| Blixing Bath | |
|---|---|
| Sodium Iron (III)-Ethylenediamine-tetraacetate | 34.0 g |
| Sodium Carbonate (monohydrate) | 11.0 g |
| Borax | 45.0 g |
| Sodium Thiosulfate | 140.0 g |
| Water to make | 1.0 l |

As is shown in Table 6, a photographic material of the present invention provides a sufficiently high density in the infrared region using a small amount of silver even when it is processed by a processing containing a blixing step. Also, when it is processed using a bleaching solution containing a ferricyanide, it provides a high amount of residual silver. In particular, a remarkable silver bleach inhibiting effect is observed when a silver bleach inhibitor and the thione compound are incorporated into the emulsion in the form of a dispersion.

While the invention has been described in detail and with reference to specific embodiments thereof, it will be apparent to one skilled in the art that various changes and modifications can be made therein without departing from the spirit and scope thereof.

What is claimed is:

1. A color photographic lightsensitive material which comprises a support having thereon
   at least one blue-sensitive silver halide emulsion layer containing a yellow dye-forming coupler,
   at least one red-sensitive silver halide emulsion layer containing a cyan dye-forming coupler,
   at least one green-sensitive silver halide emulsion layer containing a magenta dye-forming coupler and
   at least one light-sensitive silver halide emulsion layer containing
   (a) at least one non-diffusible silver bleach inhibitor selected from the group consisting of (i) a nitrogen-containing heterocyclic compound having a thioether bond represented by the following general formula (I):

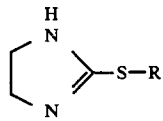

wherein R is an alkyl group having not less than 12 carbon atoms, with the alkyl group being both substituted or unsubstituted; and (ii) a nitrogen-containing heterocyclic compound represented by the following general formula (II):

wherein $Z_1$ is an atomic group necessary for forming a substituted or unsubstituted pyridine nuclei, imidazole nuclei or quinoline nuclei, $X^-$ is an anion, $R_1$ is a group having not less than 11 carbon atoms and is selected from the group consisting of (a) an alkyl group, (b)

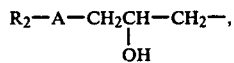

(c)

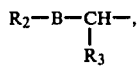

and (d)

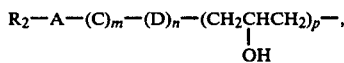

$R_2$ is an alkyl or alkylaryl group, $R_3$ is a hydrogen atom or a methyl group, A is —O—, —S—, —COO— or —NCH$_3$—, B is —O—, —COO—, —CONH— or —CONHC$_2$H$_4$CONH—, C is an oxyalkylene group, D is —CH$_2$CH$_2$— or —O—, m is an integer of 1 to 40, n is 0 or 1, and p is 0 or 1; in combination with (b) at least one heterocyclic thione compound having a thione group which is incapable of forming a mercaptan and which is a compound represented by the following general formula (III):

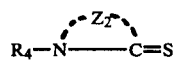

wherein $R_4$ represents an aliphatic group, an aryl group or a heterocyclic group, and $Z_2$ represents an atomic group necessary to form a heterocyclic ring.

2. The color photographic light-sensitive material as claimed in claim 1, wherein said heterocyclic ring containing $Z_2$ in the general formula (III) is selected from the group consisting of a thiazolidine-2-thione ring, an imidazolidine-2thione ring, a selenazolidine-2-thione ring, a 1,3,4-tiadiazoline-2-thione ring, a 1,3,4-selenadizoline-2-thione ring, a 4-thiazoline-2-thione ring, a 4-selenazoline-2-thione ring, a 1,2-dihydropyridine-2-thione ring, a benzothiazoline-2-thione ring, a benzoxazoline-2-thione ring, a benzimidazoline-2-thione ring, a benzoselenazoline-2-thione ring and a 1,2-dihydroquinoline-2-thione ring.

3. The color photographic light-sensitive material as claimed in claim 1, which comprises a support having coated thereon
   a blue-sensitive silver halide emulsion layer containing a yellow dye-forming coupler,
   a red-sensitive silver halide emulsion layer containing a cyan dye-forming coupler,
   a green-sensitive silver halide emulsion layer containing a magenta dye-forming coupler and
   a light-sensitive silver halide emulsion layer containing
   (a) at least one non-diffusible silver bleach inhibitor represented by the general formulae (I) or (II) and
   (b) at least one heterocyclic thione compound represented by the general formula (III), in this order from the support.

4. The color photographic lightsensitive material as claimed in claim 1, which comprises a support having coated thereon
   a blue sensitive silver halide emulsion layer containing a yellow dye-forming coupler,
   a red-sensitive silver halide emulsion layer containing a cyan dye-forming coupler,
   a green-sensitive silver halide emulsion layer containing a magenta dye-forming coupler, in this order from the support, and
   a light-sensitive silver halide emulsion layer containing
   (a) at least one silver bleach inhibitor represented by the general formulae (I) or (II) and
   (b) at least one heterocyclic thione compound represented by the general formula (III),
   said layer being positioned between said blue-sensitive silver halide emulsion layer containing a yellow dye-forming coupler and said red-sensitive silver halide emulsion layer containing a cyan dye-forming coupler or between said red-sensitive silver halide emulsion layer containing a cyan dye-forming coupler and said green-sensitive silver halide emulsion layer containing a magenta dye-forming coupler.

* * * * *